US012616377B2

(12) United States Patent

Zhu et al.

(10) Patent No.: US 12,616,377 B2
(45) Date of Patent: May 5, 2026

(54) TRANSPONDER TRACKING AND ULTRASOUND IMAGE ENHANCEMENT

(71) Applicant: DeepSight Technology, Inc., Santa Clara, CA (US)

(72) Inventors: Jiangang Zhu, St. Louis, MO (US); Mucong Li, St. Louis, MO (US); Linhua Xu, University City, MO (US); Michael Hazarian, San Jose, CA (US)

(73) Assignee: DEEPSIGHT TECHNOLOGY, INC., Santa Clara, CA (US)

( * ) Notice: Subject to any disclaimer, the term of this patent is extended or adjusted under 35 U.S.C. 154(b) by 0 days.

(21) Appl. No.: 18/382,984

(22) Filed: Oct. 23, 2023

(65) Prior Publication Data

US 2024/0423482 A1 Dec. 26, 2024

Related U.S. Application Data

(60) Provisional application No. 63/510,079, filed on Jun. 23, 2023, provisional application No. 63/522,793, filed on Jun. 23, 2023, provisional application No. 63/522,994, filed on Jun. 23, 2023.

(51) Int. Cl.
| | |
|---|---|
| *A61B 5/00* | (2006.01) |
| *A61B 5/06* | (2006.01) |
| *A61B 8/08* | (2006.01) |
| *G01H 9/00* | (2006.01) |
| *G01S 15/89* | (2006.01) |

(52) U.S. Cl.
CPC .............. *A61B 5/0097* (2013.01); *A61B 5/06* (2013.01); *A61B 8/0841* (2013.01); *G01H*

9/004 (2013.01); *G01S 15/8965* (2013.01); *G01S 15/8968* (2013.01)

(58) Field of Classification Search
CPC ....... A61B 5/0097; A61B 5/06; A61B 8/0841; G01H 9/004; G01S 15/8965; G01S 15/8968
See application file for complete search history.

(56) References Cited

U.S. PATENT DOCUMENTS

| | | | |
|---|---|---|---|
| 5,961,463 | A | 10/1999 | Rhyne et al. |
| 8,560,048 | B2 | 10/2013 | Rourke et al. |
| 10,595,816 | B2 | 3/2020 | Tahmasebi Maraghoosh et al. |
| 2008/0128506 | A1 | 6/2008 | Tsikos et al. |
| 2012/0059259 | A1 | 3/2012 | Emery et al. |
| 2015/0133787 | A1 | 5/2015 | Wegner |

(Continued)

FOREIGN PATENT DOCUMENTS

| | | |
|---|---|---|
| WO | 2021055823 A2 | 3/2021 |
| WO | 2023/060235 A1 | 4/2023 |

OTHER PUBLICATIONS

Wang et al. "A Comprehensive Study of Optical Fiber Acoustic Sensing," IEEE Access, vol. 7, pp. 85821-85837, 2019, doi: 10.1109/ACCESS.2019.2924736. (Year: 2019).*

(Continued)

*Primary Examiner* — Amelie R Davis
(74) *Attorney, Agent, or Firm* — Kilpatrick Townsend & Stockton LLP

(57) ABSTRACT

A transponder is used for tracking a position of a distal end of a medical device in an ultrasound image and/or enhancing an ultrasound image.

24 Claims, 7 Drawing Sheets

(56) References Cited

U.S. PATENT DOCUMENTS

| | | | |
|---|---|---|---|
| 2016/0038119 A1* | 2/2016 | Desjardins | A61B 8/4444 |
| | | | 600/424 |
| 2016/0045184 A1 | 2/2016 | Courtney et al. | |
| 2017/0172539 A1 | 6/2017 | Vignon et al. | |
| 2017/0307741 A1 | 10/2017 | Ralston et al. | |
| 2019/0216423 A1* | 7/2019 | Ko | A61B 8/463 |
| 2021/0055473 A1* | 2/2021 | Shnaiderman | G01L 11/025 |
| 2021/0251605 A1* | 8/2021 | Desjardins | A61B 8/4483 |
| 2021/0401398 A1 | 12/2021 | Ma et al. | |

OTHER PUBLICATIONS

"BD Cue™ Needle Tracking System with BD Prevue™ II Vascular Access System", YouTube, retrieved from internet Sep. 12, 2023 from, "https://www.youtube.com/watch?v=YqCXAH3gzkg".

"Onvision® Needle Tip Tracking Demonstration Video", YouTube, retrieved from internet on Sep. 12, 2023, "https://www.youtube.com/watch?v=2lxvrwsG39c".

PCT App. No. "PCT/US22/77762 International Search Report and Written Opinion", 22 pages.

Baker, et al., "Intraoperative Needle Tip Tracking with an Integrated Fibre-Optic Ultrasound Sensor", Special Issue Fibre-Optic Devices for Minimally Invasive Medical Procedures, retrieved from internet Sep. 12, 2023 at https://www.mdpi.com/1424-8220/22/23/9035, Nov. 22, 2022, 29 pages.

Kåsine, et al., "Needle tip tracking for ultrasound-guided peripheral nerve block procedures—an observer blinded, randomised, controlled, crossover study on a phantom model", Acta Anaesthesiol Scand. retrieved from internet on Sep. 12, 2023, "https://onlinelibrary.wiley.com/doi/epdf/10.1111/aas.13379", 2019, 8 pages.

Mari, et al., "Needle-tip localization using an optical fibre hydrophone", Proceedings of SPIE vol. 8938—The International Society for Optical Engineering, Jan. 2014, 8 pages.

Monifi, et al., "Ultrasound Sensing Using a Fiber Coupled Silica Microtoroid Resonator Encapsulated in a Polymer", 2013 IEEE Photonics Conference, Bellevue, WA, USA, doi: 10.1109/IPCon.2013.6656511, 2013, pp. 2015-2016.

Wei, et al., "High-Frequency Ultrasonic Sensor Arrays Based on Optical Micro-ring Resonators", Proc. SPIE 10600, Health Monitoring of Structural and Biological Systems XII, 1060003, Mar. 27, 2018, 8 pages.

Xia, et al., "Coded Excitation Ultrasonic Needle Tracking: an in vivo study", Medical Physics 43, 4065; doi 10.1118/1.4953205, 2016, 10 pages.

EP International Search Report and Written Opinion for PCT/US2024/035062 mailed Sep. 16, 2024.

Mathews, Sunish J. et al., "Ultrasonic Needle Tracking With Dynamic Electronic Focusing", Ultrasound in Medicine and Biology, New York, NY, vol. 48, No. 3. Dec. 30, 2021; pp. 520-529.

* cited by examiner

500

600

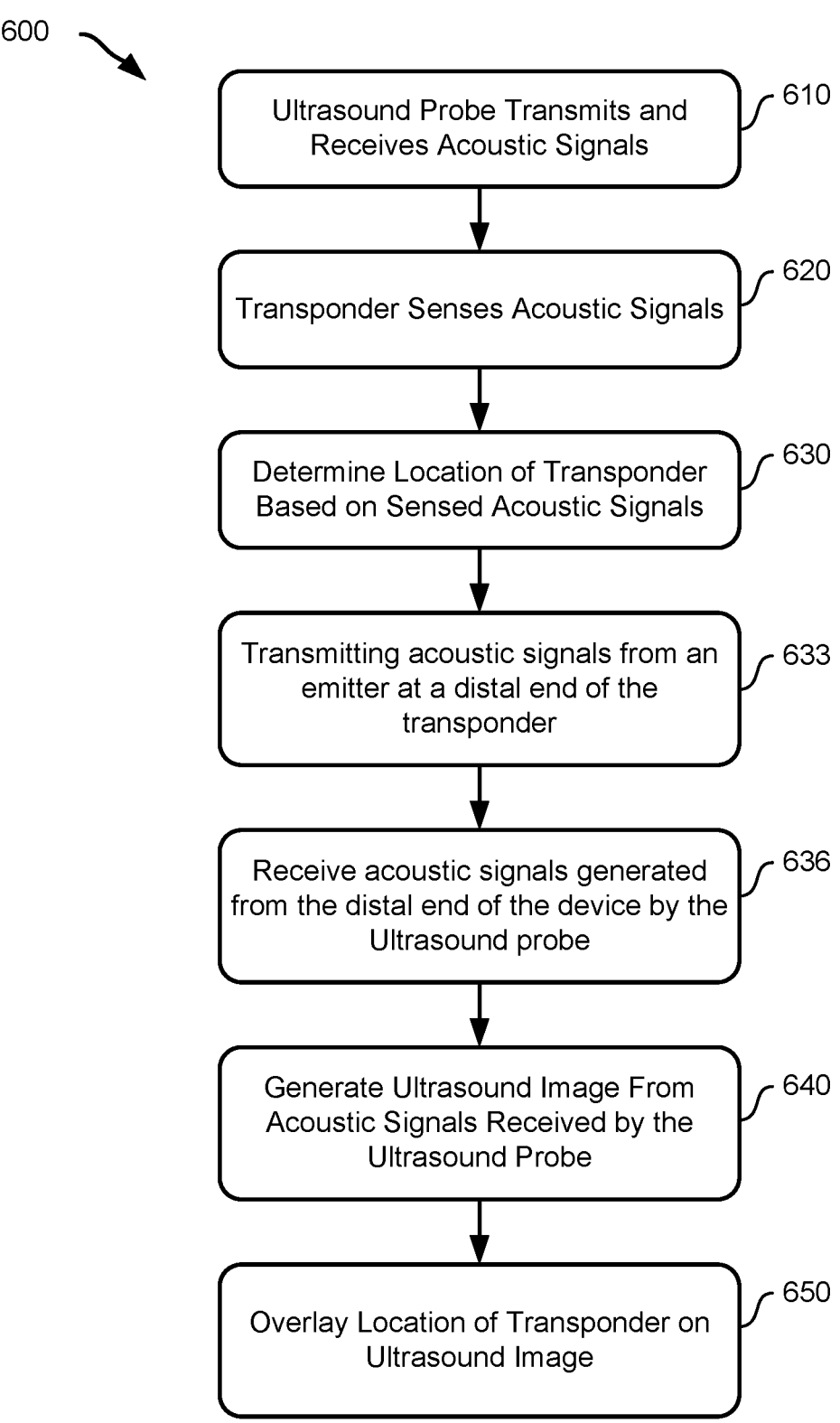

610
Ultrasound Probe Transmits and Receives Acoustic Signals

620
Transponder Senses Acoustic Signals

630
Determine Location of Transponder Based on Sensed Acoustic Signals

633
Transmitting acoustic signals from an emitter at a distal end of the transponder 636
Receive acoustic signals generated from the distal end of the device by the Ultrasound probe 640
Generate Ultrasound Image From Acoustic Signals Received by the Ultrasound Probe 650
Overlay Location of Transponder on Ultrasound Image

Ultrasound Probe Transmits Acoustic Pulses    710

Fiber Sensor Senses Acoustic Signals    715

Ultrasound Probe Senses Acoustic Signals    720

Generate Ultrasound Image From Acoustic Signals Received by the Ultrasound Probe    730

Enhance the Ultrasound Image Using Data From the Fiber Sensor    740

TRANSPONDER TRACKING AND ULTRASOUND IMAGE ENHANCEMENT

CROSS REFERENCE TO RELATED APPLICATIONS

This application claims priority to U.S. Provisional Application No. 63/522,944, filed Jun. 23, 2023, entitled, "TRANSPONDER TRACKING AND ULTRASOUND IMAGE ENHANCEMENT," U.S. Provisional Application No. 63/522,793, filed Jun. 23, 2023, entitled "OPTICAL FIBER WITH AN ACOUSTICALLY SENSITIVE FIBER BRAGG GRATING AND ULTRASOUND SENSOR INCLUDING THE SAME," and U.S. Provisional Application No. 63/510,079, filed Jun. 23, 2023, entitled "FIBER OPTICAL SENSOR SYSTEM FOR ULTRASOUND SENSING AND IMAGING," which are incorporated by reference for all purposes.

The following U.S. patent applications are being filed concurrently with this application and are incorporated by reference for all purposes:

- U.S. application Ser. No. 18/492,593, filed on Oct. 23, 2023, entitled "FIBER OPTICAL SENSOR SYSTEM FOR ULTRASOUND SENSING AND IMAGING";
- U.S. Provisional Application No. 63/592,482, filed on Oct. 23, 2023, entitled "TRANSDUCER ARRAY WITH FIBER SENSORS-FIBER-OPTICAL SENSOR SYSTEM FOR ULTRASOUND SENSING AND IMAGING"; and
- U.S. Provisional Application No. 63/545,327, filed on Oct. 23, 2023, entitled, "MINIATURE MIXED ARRAY IMAGING PROBE".

BACKGROUND

The present application generally relates to ultrasound imaging and more particularly relates to transponder tracking and ultrasound image enhancement. Acoustic imaging may be used for both medical and non-medical applications. One well-known example of acoustic imaging is ultrasound imaging, which is non-invasive and allows viewing of soft tissues and surrounding anatomy. Ultrasound imaging may also be used to view the location of various medical devices in situ, such as needles, scopes, or catheters.

However, the transducers used in conventional ultrasound probes may be limited in output and thus produce non-optimal ultrasound images, resulting in an inability to accurately track the location of devices. Accordingly, there is a need for improved methods and systems for tracking and image enhancement.

SUMMARY

Various examples are described for transponder tracking and ultrasound image enhancement. These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIGS. 5 and 6 show example methods for transponder tracking and ultrasound image enhancement.

DETAILED DESCRIPTION

Figure 1:
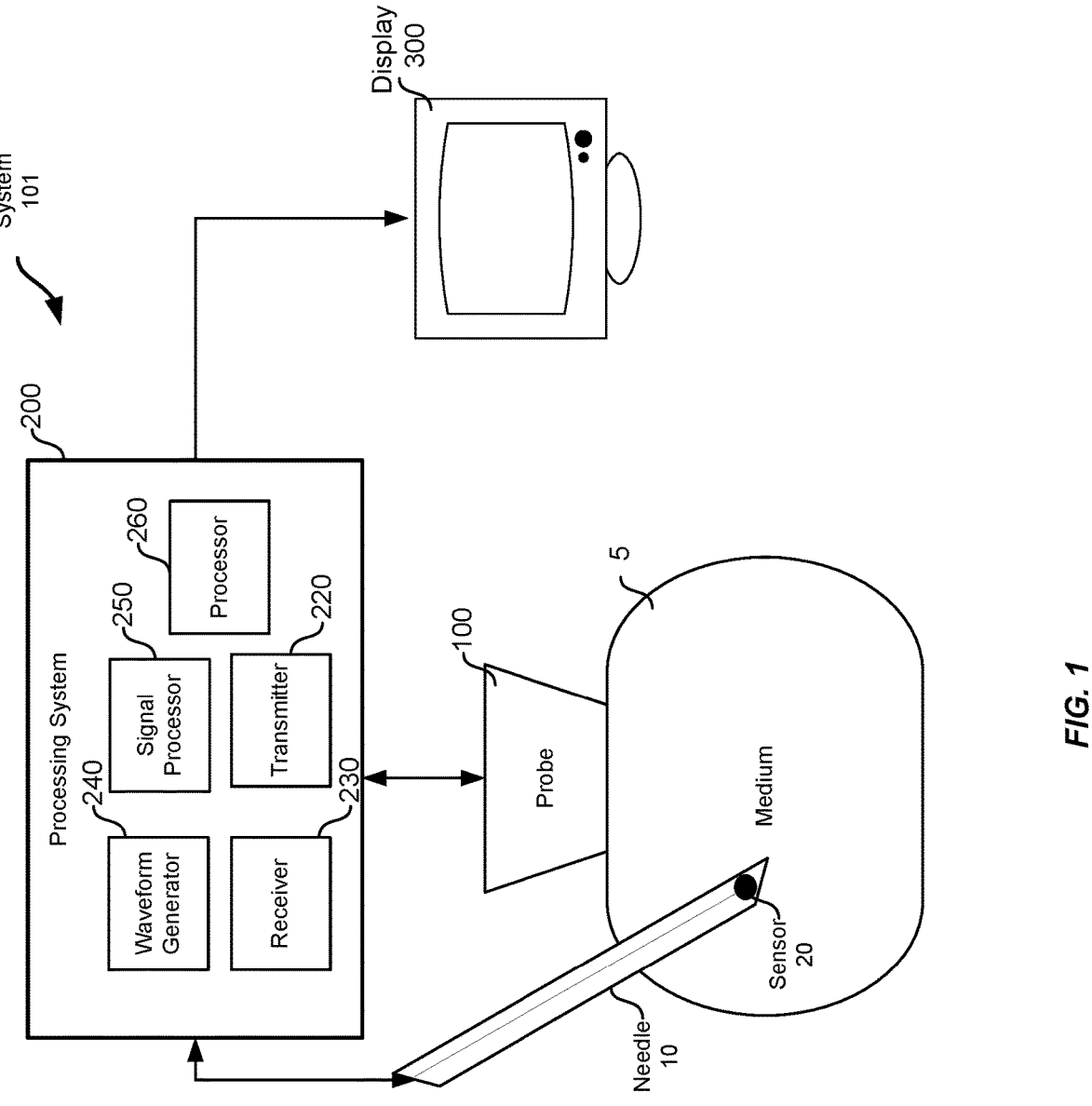
FIGS. 1, 2A, and 2B show example systems for transponder tracking and ultrasound image enhancement.

Examples are described herein in the context of transponder tracking and ultrasound image enhancement. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions can be made in order to achieve the developer's specific goals, such as compliance with application-and business-related constraints, and that these specific goals will vary from one implementation to another and from one developer to another.

The following commonly owned patent applications disclose various methods and systems for ultrasound beamforming and image processing: U.S. application Ser. No. 18/032,953, filed Apr. 20, 2023, titled Image Compounding for Mixed Ultrasound Sensor Array; U.S. application Ser. No. 18/205,081, filed Mar. 7, 2023, titled Synthetic Aperture Imaging Systems and Methods Using Mixed Arrays; U.S. application Ser. No. 18/901,073, filed Dec. 29, 2022, titled Acousto-Optic Harmonic Imaging with Optical Sensors; PCT Application PCT/US2022/077762, filed Oct. 7, 2022, titled Ultrasound Beacon Visualization with Optical Sensors; PCT Application PCT/US2022/041250, filed Aug. 23, 2022, titled Multi-Dimensional Signal Detection with Optical Sensor; and PCT Application PCT/US2022/018515, filed Mar. 2, 2022, titled Acoustic Imaging and Measurements Using Windowed Nonlinear Frequency Modulation Chirp.

Object visualization, tracking, and location in medical applications may be important aspects for performing medical procedures in a safe and reliable manner. Therapeutic and diagnostic medical applications include ultrasound imaging as well as sensing (e.g., tracking, visualizing, and monitoring) of objects (e.g., needle, catheter, guidewire, etc.) during guided needle access, biopsy, aspiration, delivery of drugs, biologics, anesthesia or other therapeutics, catheterization, minimally invasive procedures, ablation, cauterization, placement or moving of objects, tissue, cutting, sectioning, and other medical procedures. Procedures and applications in the following disciplines are examples of the wide usage and need for accurate guidance and imaging during diagnostic and therapeutic procedures: anesthesia, cardiology, critical care, dermatology, emergency medicine, endocrinology, gastroenterology, gynecology and obstetrics, hepatology, infectious diseases, interventional radiology, musculoskeletal medicine, nephrology, neurology, oncology, orthopedics, pain management, pediatrics, plastic and reconstructive surgery, urology, vascular access, and other disciplines.

In non-medical applications, ultrasound is used in industrial applications for defect detection and microparticle particle sorting among other applications, non-destructive testing, structural testing, geological applications including mining and drilling operations, and underwater marine applications. Such applications are consistent with embodiments described herein.

Objects for tracking, visualization, and location may include any type of medical device that travels or is located within the body of a subject. For instance, medical practitioners visualize and track a needle tip while conducting a biopsy to ensure safety. In such instances, accurate needle tip visualization or tracking may help to prevent or reduce unintentional vascular, neural, tissue or visceral injury. Similarly, it may be helpful to visualize, track, or locate needles, endoscopes, cannulas, laparoscopic tools or other medical device tools when performing medical procedures such as, but not limited to, aspiration of fluid; injections of joints, tendons, and nerves with drugs or biologics; biopsy of fluids or soft tissue masses; aspiration and lavage of calcifications; removal of tissue, organs or foreign bodies, placement of a stent, filter, valve, permanent, temporary or biodegradable implant, shunt or drain, injections for anesthesia, inserting vascular access devices used for infusion therapies, ablation procedures, performing the Seldinger technique or catheterization to gain access to blood vessels and/or other organs in a safe manner. Visualization and tracking may be advantageous in minimally invasive surgical and open surgical procedures, especially when the area of interest is hidden or obstructed by tissue, blood or fluids.

In one example system for an ultrasound guided intervention, an ultrasound transponder is coupled to a medical device, such as a needle, that is to be inserted into the tissue or body lumen of a patient, such as a human or animal. The transponder may be an ultrasound receiver or transmitter or a combination of both. The example transponder includes a sensor, such as a point sensor, a line sensor, or a sensor formed in some other known shape. The transponder may be coupled to one end of the needle, such as the distal end of a needle, which is the end that first penetrates the tissue or enters a body cavity or lumen. In some examples, multiple transponders are coupled to the needle or medical device. For instance, one transponder may be coupled to the distal end while another is coupled to the mid-point of the needle or other area that will provide positional information helpful during the procedure. The transponder may also be formed in an array (e.g., 1D, 1.5D, 2D etc.) that may be linear, annular, or curved depending on a form factor of the needle or medical tool to which the transponder is secured and/or the imaging area of interest. In embodiments where the transponder includes a transmitter, the transmitter may or may not be integral with the sensor and may be on the medical device being tracked or on a component of the medical device delivery system, such as a catheter, cannula, or endoscope.

The example system also includes an ultrasound probe. The ultrasound probe includes an array of transducers that output and receive a plurality of acoustic beamforming pulses or signals. The example system also includes a computer processor, display and associated electronics for receiving data from the ultrasound probe and utilizing the data to generate an ultrasound image.

The transponder in the example system is also in communication with a processor and associated electronics. When the transponder senses the acoustic pulses from the probe, it provides information to the processor that may be used to determine the location of the transponder in relation to the probe. For example, the location of the transponder may be determined by triangulation or by coherent image formation. The location of the transponder sensor can then be used to display the transponder in conjunction with the ultrasound image, e.g., the transponder location overlayed on the ultrasound image.

In some embodiments, the transponder may also work as a receiver that detects scattered acoustic signals and/or tissue harmonics. When the transponder is positioned within an insonified imaging area of interest, the transponder may detect weak scattered or harmonic signals that are unable to propagate very far (e.g., acoustic signals that have too low of signal-to-noise ratio to be detected by probe 100 in FIG. 1). The transponder transmits detection of these signals to the processor. The processor uses the signals detected by the transponder to reconstruct the ultrasound image of the anatomy and insonified region surrounding the transponder (e.g., with a delay and sum beamforming method). This allows the ultrasound processor to generate an image of better quality than one generated solely based on signals detected by the ultrasound probe (e.g., probe 100 in FIG. 1). Accordingly, the transponder can be used for tracking a medical device and/or enhancing an acoustic image.

In some embodiments, the transponder also includes an emitter, such as a transducer, which can transmit a plurality of ultrasound pulses. The ultrasound probe receives these pulses and transmits corresponding signals to the processor. The transponder sensor may also receive reflections of these ultrasound pulses and transmit corresponding signals to the processor. The processor uses the signals in conjunction with the location of the transponder to coherently reconstruct the ultrasound image of the anatomy surrounding the transponder. This allows the ultrasound processor to generate an image of better quality than one generated solely based on the pulses emitted by the ultrasound probe. It is to be understood that the transponder does not include an emitter in some embodiments.

This illustrative example is given to introduce the reader to the general subject matter discussed herein and the disclosure is not limited to this example. The following sections describe various additional non-limiting examples and examples of transponder tracking and ultrasound image enhancement.

Turning to FIG. 1, FIG. 1 is an example of a system 101 for ultrasound visualization of a transponder, such as a transponder coupled to a medical device. System 101 may be used for ultrasound transponder visualization of a medical device, such as needle 10 present in a media 5 (e.g., body tissue, body cavity, body lumen). However, it should be understood that in other examples the system 101 may be used for ultrasound visualization of other medical devices such as a catheter, a guidewire, an intravenous (IV) line, an endoscope, a trocar, an implant, combinations thereof. System 101 may also be used to enhance visualization of aspects present in the medium 5, such as, for example, organs, vessels, tissue, tumors, other anatomical structures, other medical devices, or implants. Further, while the examples that follow describe determining the location of a medical device, examples of this disclosure may be utilized to locate non-medical devices as well, such as applications in non-medical industries that use ultrasound imaging and/or tracking.

In some examples, the system 101 may comprise a processing system 200 in communication with an ultrasound probe 100, a transponder in the form of an optical sensor 20 coupled to a needle 10, and a display 300. In some examples, the needle 10 may comprise more than one sensor 20 or combinations of sensors 20. While the sensor 20 is shown in FIG. 1 as a single element, there may be separate multiple elements arranged adjacent or spaced apart from each other or in an array form factor. During a procedure, the needle 10 may be inserted into the medium 5. The optical sensor 20 (e.g., coupled with needle 10) is arranged to be moved independently from motion of the probe 100.

In use, the probe 100 may be placed adjacent to the medium 5 (e.g., placed externally over body tissue) to emit and receive ultrasound pulses, which may also be referred to as ultrasound signals. The area of the medium receiving the ultrasound signals may be referred to as the insonified region. In some examples, the probe 100 may be in vivo, such as intravascular ultrasound (IVUS), endobronchial ultrasound (EBUS), or endoscopic ultrasound (EUS) (e.g., tracking a needle or other device that extends out of the distal end of a catheter or endoscope such as for biopsy). In some examples, the probe 100 may include an ultrasound array with one or more elements (e.g., transducers) to output (e.g., generate) acoustic pulses and/or receive acoustic signals (e.g., echo signals) corresponding to the acoustic pulses. For example, the ultrasound array may include one or more elements (e.g., transducers) configured to emit a set of acoustic beamforming pulses (e.g., ultrasound signals) and/or receive a set of acoustic beamforming signals (e.g., ultrasound echoes) corresponding to the set of acoustic beamforming pulses. The set of beamforming signals that correspond to the set of beamforming pulses may be used to generate ultrasound images. In some examples, the medium 5 may comprise a non-linear medium such as, for example, a body tissue. In some examples, the transducer may be a linear array on the distal facing end of the catheter that is angled in close proximity to, e.g., abutting, the body tissue. The array may include acoustic energy generating (AEG) elements arranged side-by-side in a linear, annular, or convex configuration to form the array that may be front or side firing, as is well known for EBUS, IVUS and EUS devices.

In some examples, the elements of the probe 100 may be arranged as an array such as an ultrasound array. For example, probe 100 may include one or more acoustic energy generating (AEG) transducers, such as one or more of a piezoelectric transducer, a lead zirconate titanate (PZT) transducer, a polymer thick film (PTF) transducer, a polyvinylidene fluoride (PVDF) transducer, a capacitive micromachined ultrasound transducer (CMUT), a piezoelectric micromachined ultrasound transducer (PMUT), a photoacoustic transducer, a transducer based on single crystal materials (e.g., LiNb03(LN), Pb(Mg113Nb213)-PbTiQ3 (PMN-PT), and Pb(In112Nb112)-Pb(Mg113Nb213)PbTiQ3 (PIN-PMN-PT)), combinations thereof, and the like. It should be understood that the probe 100 may include a plurality of any of the transducer types. In some examples, the ultrasound array may include the same type of elements. Alternatively, the ultrasound array may include different types of elements. The probe 100 can be a traditional ultrasound probe with an acoustic energy generating transmitter and receiver, or the probe 100 can be an acoustic-optical probe (e.g., as described in application 63/450,554, filed on Mar. 7, 2023, titled Mixed Array Imaging Probe," U.S. application Ser. No. 17/990,596, filed on Nov. 18, 2022 titled "Mixed Ultrasound Transducer Arrays," and U.S. application Ser. No. 17/244,605 filed on Apr. 29, 2021 titled "Modularized Acoustic Probe"). In some examples that include the acoustic-optical probe, an ultrasound array may include one or more optical sensors, such as an interference-based optical sensor, which may be one or more of an optical interferometer, optical cavity, optical resonator (e.g., whispering gallery mode (WGM) resonators among others), birefringent sensor, or an optical fiber end facet with an acoustic-responsive structure.

One or more optical sensors 20 are arranged at or near the end of the needle 10 and may be configured to receive acoustic signals corresponding to the acoustic pulses emitted by the transducers of the probe 100. The optical sensors 20 convert received acoustic signals into optical signals that may be transmitted to the processing system 200 via an optical fiber or other suitable waveguide. The fiber optical sensors may be disposed at the end of an optical fiber, adjacent an end of an optical fiber or at a diagnostic or therapeutic relevant location on the medical device to create a sensor fiber. These fiber optical sensors can be point sensors or line sensors. The fiber optical sensors include resonant structures, including, but not limited to Fabry-Perot (FP) resonators, whispering-gallery-mode resonators, optical cavity, and photonic crystal resonators; interferometers, including, but not limited to MZI, phase-shift coherent interferometers, and self-mixing interferometers; acoustic induced birefringent polarization sensors; fiber end facets with acoustic responsive structures such as metasurfaces including patterns of small elements arranged to change the wavefront shape of the acoustic signals and maximize the collection of acoustic signals, low-dimensional materials with special optomechanical features that more prone to deformation; and plasmonic structure patterned to amplify light-matter interactions. In addition to operating as an optical sensor, the fiber end facet structures can also be added to the other fiber optical sensors to further enhance acoustic response. These optical structures are configured to respond to acoustic (such as ultrasound) signals. Reponses to acoustic signals in interference-based fiber optical sensors may be due to the photo-elastic effect and/or physical deformation of the structures. When subject to acoustic signals, the resonant structures, or interferometer structures or fiber end facets with acoustic responsive structures, are subject to mechanical stress and/or strain from the alternating pressures of the acoustic signal sound waves. This mechanical stress and/or strain may change the optical properties of the optical sensor structures due to the photo-elastic effect and may also cause changes or deformations in the physical structure of resonator. With polarization-based sensors, the polarization changes when the light is subjected to acoustic signals. When coupled to a light source (e.g., a laser light source, a broadband light source (e.g., a lamp or LED) or other suitable light source) via an optical waveguide (e.g., an optical fiber), the effect of acoustic signals on the optical sensor structures may be measured due to changes in the light returned from the optical sensor structures via the optical waveguide. More details of these fiber sensors can be found in concurrently filed application U.S. Application Ser. No. 18/492,593, filed on Oct. 23, 2023, entitled "FIBER OPTICAL SENSOR SYSTEM FOR ULTRASOUND SENSING AND IMAGING".

In some examples, the probe 100 may be configured to receive acoustic beamforming signals reflected in response to interactions of the acoustic beamforming pulses with the aspects present in the medium 5, with the medium 5, and/or with the needle 10. The probe 100 may be configured to transmit to the processing system 200 signals corresponding to the received acoustic beamforming signals.

The processing system 200 may include a transmitter 220, a receiver 230, a waveform generator 240, and one or more processors (e.g., a signal processor 250 and processor 260). The waveform generator 240 may be configured to generate a set of digital waveforms for acoustic beamforming pulses. One or more processors (e.g., processor 260) included in the processing system 200 may be configured to control the waveform generator 240. The waveform generator 240 may be configured to generate and send the digital waveforms to one or more of the transmitter 220 and/or a matched filter/ Weiner filter (not shown).

In some embodiments, a system comprises the optical sensor for sensing acoustic signals used for calculating a position of a device within a medium, while the optical sensor is also within the medium. The sensor can be coupled with the device (e.g., a needle) for insertion into the medium. The device can be part of a third-party system (e.g., so that the sensor provides additional capabilities to the third-party system). In some embodiments, the sensor and the device are provided as a unit to be incorporated into a third-party system (e.g., a third-party system comprising the probe 100 and processing system 200 in FIG. 1).

In the example shown in FIG. 1, the processing system 200 is configured to generate an ultrasound image based on the received acoustic beamforming signals. The received beamforming signals may be those received by the probe 100 and/or sensor 20. The processing system 200 is also configured to analyze the optical signals received from the sensor 20 to generate a transponder indicator corresponding to the location of the tip of the needle 10 in the medium 5. The ultrasound images and the transponder indicator may be optionally displayed on the display 300. Additionally or alternatively, the transponder indicator may be output as one or more of an audio signal and a haptic signal.

Although the medical device in FIG. 1 is shown to be a needle 10, it should be understood that another suitable medical device may be visualized and/or tracked using the system 101. For example, system 101 may be used to visualize and/or track various diagnostic, therapeutics and surgical medical devices, such as, but not limited to a catheter, needle, endoscope, ablation tool, cauterization tool, vacuum or suction tool, tool for grabbing or moving tissue or other objects, forceps, cutting tool, minimally invasive surgical tool, and/or open surgical tool, as the device is advanced into and/or manipulated within the medium, which may include a blood vessel, organ, tissue, cavity, and/or lumen.

Figures 2A, 2B:
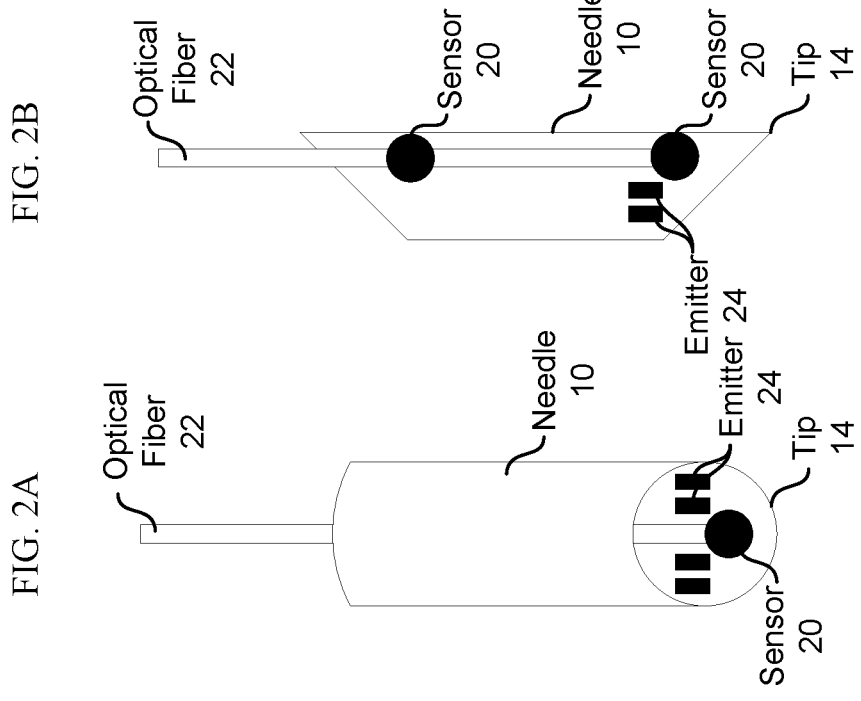

Turning to FIGS. 2A and 2B, FIGS. 2A and 2B illustrate the needle 10 in the example illustrated in FIG. 1. The optical sensor 20 shown in FIGS. 2A and 2B may be arranged on (e.g., coupled to, mounted on or in, integrated with, or otherwise located on or in) at least a part of the needle 10 to be tracked. The sensor 20 is fixedly coupled with the needle 10 so that there is no relative movement between the optical sensor 20 and the needle 10. In some examples, the medical device may include a needle 10 including a cylindrical body (e.g., barrel, tubing, lumen), an elongate member (e.g., plunger, shaft), and a distal tip. The elongate member may be configured to translate (e.g., slidably move) within the cylindrical body (e.g., the elongate member may translate within the cylindrical body). The elongate member may be coupled to any suitable actuation mechanism (e.g., actuator) configured to inject and/or withdraw fluid to and from the cylindrical body. For example, manually moving the elongate member within the cylindrical body may inject and/or withdraw fluid to and from the cylindrical body. Additionally or alternatively, the elongate member may be coupled to an actuator such as for example, a motor, to move the elongate member within the cylindrical body so as to inject and/or withdraw fluid to and from the cylindrical body. The cylindrical body may be open at one end and may taper into a distal tip (e.g., hollow tip) at the other end. In some examples, the tip of the needle 10 may include an attachment (e.g., connector) for a stem having a piercing tip configured to pierce through a predetermined medium (e.g., skin of a patient or tissue in order to obtain a biopsy sample). In some examples, the stem may be slender so as to be narrower in diameter than the needle 10. The tip may be any suitable type of tip such as Slip-Tip®, Luer-Lok®, eccentric, etc.

FIG. 2A illustrates an example of a system in which an optical sensor 20 is attached to a needle 10 at one end to facilitate needle tracking and position determination. In FIG. 2A, the optical sensor 20 may be attached to, coupled to, integrated with, or otherwise mounted on a tip (e.g., distal tip) of the needle 10. Depending upon the medical application, the needle may change its orientation with respect to the source of the ultrasound signal. Some needles may be flexible and/or may rotate as they navigate a twisting path to the treatment site, while others may change their angle of orientation to the ultrasound source. A window may be cut in the needle and the sensor secured to the needle so that acoustic signals can reach the sensor by passing through the window. The window can also cause scattering of the signals, which may also assist in the ascertaining the location of the needle in the insonified region. The optical sensor fiber may be integrated in the needle by locating it in a groove or channel on an outside or inside surface of the needle. The sensor may be sealed/fixed in the needle using acoustically transparent materials such as RTV or polymer (e.g., having an acoustic impedance matching condition to tissue). Multiple sensors may in an embodiment be positioned circumferentially around the needle or medical tool to ensure at least one sensor will be oriented sufficiently to receive ultrasound signal from the probe. Multiple sensors may also be formed into an array in a suitable form factor for the device on which they are coupled. The optical sensor 20 may be configured to detect acoustic signals generated from probe 100 in FIG. 1. The optical sensor 20 may be configured to receive the acoustic signals through a photo-elastic effect and/or a physical deformation of the optical sensor 20. For example, in the presence of acoustic pulses, light in the optical sensor 20 may undergo a spectral shift caused by changes in the refractive index and shape of the optical sensor 20. The optical sensor 20 may be configured to transmit a set of optical signals representative of the received acoustic transponder signals to a processing system (e.g., processing system 200 in FIG. 1). In some examples, the optical sensor 20 may be coupled to one or more optical waveguides 22 (e.g., optical fibers, photonic integrated circuit waveguides, or other optical transmitting channel) to transmit the set of optical signals to the processing system 200. The processing system 200 may be configured to generate a real time transponder location indicator based on the optical signals. In some examples, the transponder indicator may be representative of a position of the tip of the needle 10 and/or may be used to track the tip of the needle 10. For example, the tip of the needle 10 may be visualized and tracked based on the transponder indicator. Accordingly, a needle 10 may be reliably visualized and tracked during a medical procedure using at least a single optical sensor 20.

When a transponder sensor's location is known, the transponder signal can be used together with signals received by elements in the probe 100 for beamforming of ultrasound images, harmonics etc. The transponder can work as a receiver and/or a transmitter in such an imaging system. Transponder sensors can be useful for harmonic imaging of surroundings because transponder sensors are very close to an imaging area of interest, and a harmonic signal is usually weak or unable to propagate very far. As commonly known, tissue, bone, implants and other structures in the area being insonified can cause scattering of acoustic signals and/or tissue harmonics. The fiber sensor 20 can detect direct signals (e.g., from a probe 100) and scattered signals and/or tissue harmonics resulting from the probe 100 signals or emitter 24 signals in the insonified area surrounding the optical sensor. Additionally, visualizations can be displayed to assist the clinician, such as showing the path of the needle in the display along with whether or not the needle tip is within the plane (within the imaging slice) of the beamforming signal and allows for real time adjustment of the needle by the clinician to avoid anatomy or alter a path to the target area displayed in the ultrasound image.

The example needle 10 shown in FIG. 2A may also include at least one emitter 24 as part of the system delivering the needle, such as a catheter, cannula, endoscope or the like. The emitter may be, for example, an AEG transducer, such as a PZT transducer element or array. The example shown in FIG. 2A includes 4 emitters, but examples may include fewer or additional emitters. The emitters generate signals that can be received by transducers on the probe 100. The emitter 24 and sensor 20 may be combined in some embodiments. The signals received by the probe can be used to determine the location of the needle 10 either by triangulation or coherent image formation as described herein. The signals can also be used to enhance the ultrasound image produced by the processing system 200. For example, the processing system 200 can combine information from the signals generated by the probe 100 and by the emitter 24 coupled to the needle 10 to provide a higher quality image, particularly of structures surrounding the tip of the needle 10.

FIG. 2B illustrates a cross-sectional view of an exemplary example of a system in which two optical sensors 20 are attached to a needle 10 for tracking and/or determining a position of needle 10. As shown in FIG. 2B, a first optical sensor 20 may be arranged on a distal tip of the needle 10 while a second optical sensor 20 may be proximal to the first optical sensor 20 (e.g., arranged on an elongate member of the needle 10) or may be coupled at the mid-point or elsewhere on the needle 10. Accordingly, the first and second optical sensors 20 may be configured to receive acoustic signals generated by probe 100 in FIG. 1. The first and second optical sensors 20 (e.g., first optical sensor at the distal tip and the second optical sensor on the elongate member) may be coupled to the same waveguide 22 (e.g., optical fiber, photonic integrated circuit waveguide) to transmit (e.g., propagate) the optical signals to a processing system 200. The processing system may be configured to generate a first object indicator representative of a position of the tip of the needle 10 (e.g., where the first optical sensor is located) based on the optical signals received from the first optical sensor 20 and a second object indicator representative of a position of the elongate member of the needle 10 (e.g., where the second optical sensor is located) based on the optical signals received from the second optical sensor 20. Additionally or alternatively, the processing system may be configured to generate a single object indicator based on both a position of the tip of the needle 10 and a position of the elongate member using the first and second optical sensors 20. For example, the object indicator may comprise a vector. Accordingly, a needle 10 may be reliably visualized and tracked during a medical procedure by visualizing and tracking the tip and/or elongate member of the needle 10.

FIG. 2B also illustrates an emitter 24. The example shown in FIG. 2B illustrates 2 emitters, but examples may include fewer or additional emitters. As in FIG. 2A, the emitters generate signals that can be received by transducers on the probe 100. As in FIG. 2A, the emitter 24 and sensor 20 may be combined in some embodiments.

Although FIG. 2A illustrates a single optical sensor 20 for visualizing and tracking a needle 10 and FIG. 2B illustrates two optical sensors 20 for visualizing and tracking the needle 10, it should be readily understood that a suitable number of optical sensors may be used to visualize and track a medical device (e.g., three or more optical sensors, such as three, four, five, or more optical sensors and/or sensors configured in a linear, annular, curved or other suitable array). These optical sensors may be attached to, coupled to, integrated with, or otherwise mounted on a suitable part of a medical device/instrument. For example, using three optical sensors on a single needle 10 (e.g., one at the needle tip, and two along the elongate member of the needle) may facilitate tracking of a bend of the needle 10 in addition to visualizing and tracking the position of the needle tip. As discussed above, the system 101 in FIG. 1 is described and depicts needle tracking solely for illustrative purposes. It should be readily understood that any other object (e.g., end effector, catheter, guidewire, endoscope, trocar, implant) may be visualized and/or tracked using the systems and methods described herein.

Figure 4:
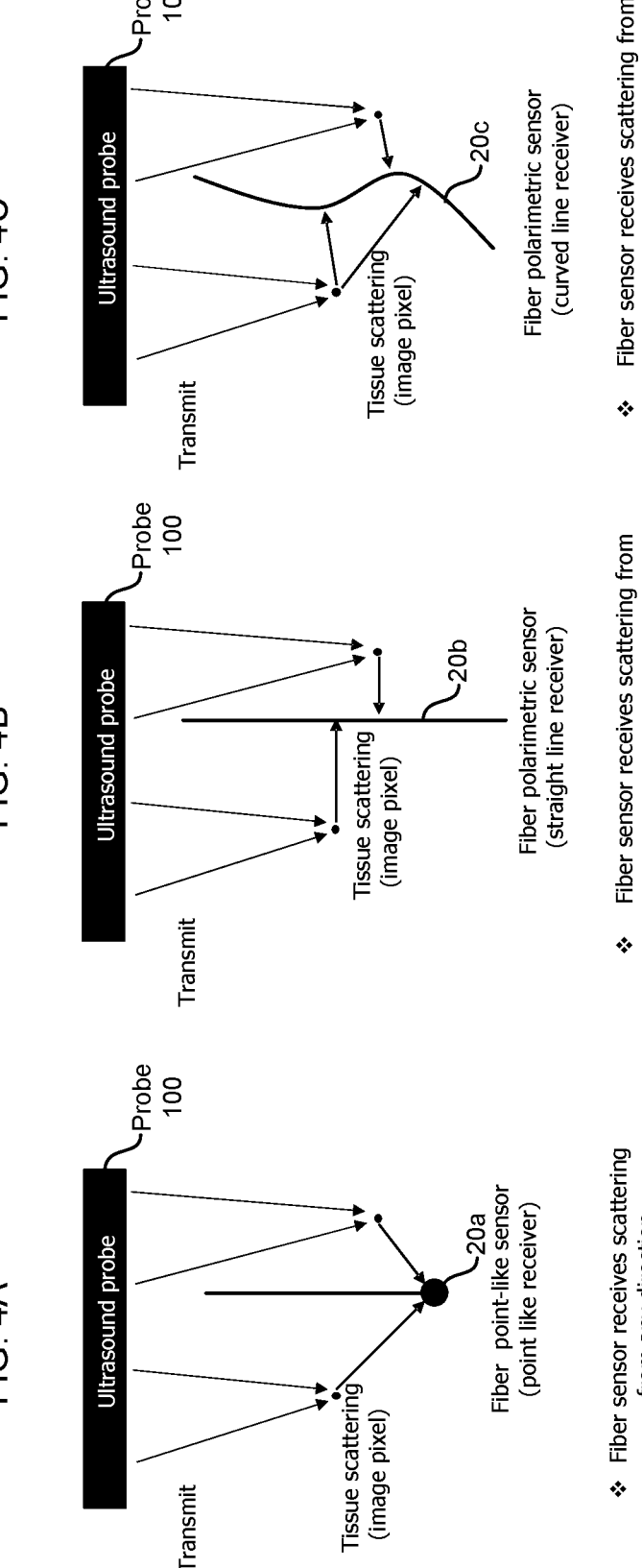
FIGS. 4A, 4B, and 4C provide examples of fiber sensors detecting acoustic signals as a point sensor or a line sensor.

The transponder can include an interferometer sensor, a resonator sensor, fiber end facet with acoustic responsive structures, and/or a polarization (birefringence) sensor (e.g., as described in concurrently filed Application titled, "FIBER OPTICAL SENSOR SYSTEM FOR ULTRASOUND SENSING AND IMAGING"). The fiber end facet structures may include acoustically responsive microstructures, such as metasurfaces including patterns of small elements arranged to change the wavefront shape of the acoustic signals and maximize the detection of acoustic signals, acoustically responsive low-dimensional materials with optomechanical features selected to optimize acoustic response (e.g., features that are more prone to deformation when receiving acoustic signals, exhibit greater material responses to acoustic signals) and plasmonic structures patterned to amplify light-matter interactions. Plasmonic structures may locally amplify incident light due to their plasmonic resonance. The transponder can be used to locate a device's location and/or orientation while a fiber sensor is mounted on the device. The device can be a needle, catheter, endoscope, surgical tool, biopsy tool, etc. Previously described transponder sensors (e.g., sensor 20 in FIG. 2) may be "point like" in that the sensor 20 has a dimension close to or smaller than a certain feature size that is meaningful for an application, such as a wavelength of an acoustic signal or a diameter of a needle (e.g., sensor 20a in FIG. 4A). The fiber sensor using polarization (birefringence) may in addition to being "point like," may also be "line like" or "line type." (e.g., sensors 20b and 20c in FIGS. 4B and 4C). A line type sensor can use a polarization sensitive detection mechanism in an optical fiber. When an acoustic signal hits (e.g., is incident on) the optical fiber, the acoustic signal changes stress within the optical fiber material (e.g., in two axes), dependent on a direction of the acoustic signal, and the acoustic signal induces a birefringent effect in the optical fiber. Light passing through the optical fiber will experience a polarization change, since light polarization components that align with the two birefringent axes will experience different phase retardations. Such polarization change induced by acoustic signals (e.g., ultrasound) can be detected by a polarization analyzer (such as a polarizer) by detecting the polarization change in light passed through the optical fiber. Thus, an acoustic signal can be sensed using polarization of light within a waveguide (e.g., an optical fiber). In a line type fiber sensor, acoustic signals can be detected strongest when the acoustic signal is propagated in a direction orthogonal to (e.g., in a direction orthogonal to a tangent of) the optical fiber (e.g., see FIG. 4B and FIG. 4C). The orthogonal direction may also be referred to as lateral, substantially lateral, or from any direction relative to the axis of the optical fiber. Many sections, or portions, of the optical fiber can be sensitive to an acoustic signal, because the acoustic signal changes the polarization state of light within the sections of the optical fiber. Changes from many sections of the optical fiber will collectively change polarization of light within the optical fiber and thus collectively change an output signal. Detection of lateral signals at multiple points along the length of the optical fiber may enhance an ability to track and/or locate the sensor fiber 604 when it is disposed within an insonified region (e.g., during a medical procedure). A line type fiber sensor can be straight, 20b, or be arranged in a shape, 20c, to facilitate different applications. For example, the fiber sensor can be curved to form a "focused" type sensor that (e.g., optimally) detects ultrasound coming from a designed focusing spot or conform to the shape of the medical tool/device. It is also to be understood that a line-like sensor is not limited to a fiber sensor using birefringence, as multiple point like optical sensors may be arranged to form a line like arrangement.

Detection of lateral signals at multiple points along the length of the sensors 20b and 20c may enhance an ability to track and/or locate the sensor fibers when it is disposed within a medium (e.g., within a human body during a medical procedure). For example, as shown in FIGS. 4B and 4C, multiple signals incident along the length of the sensor fibers may enhance an ability to determine the location of different portions of the sensor fibers along its length and therefore to identify the location of the entire sensor fibers 20b and 20c, and not just a tip region like 20a. For example, as shown in FIGS. 4B and 4C, multiple signals incident along the length of the sensor fibers 20b and 20c may enhance an ability to determine the location of different portions of the sensor fibers 20b and 20c and therefore to identify curvature of the sensor fibers 20c with greater accuracy.

To couple a fiber sensor in a device, a groove or channel may be fabricated on a device inner or outer surface to allow the optical fiber to be embedded in, the optical fiber can be glued on the surface directly, and/or the optical fiber can be covered in a protective material layer, such as a polymer coating or other acoustically transparent material. The line type fiber sensor 20b or 20c can be used in lieu of, or in combination with, one or more point like 20a sensors.

In some embodiments, an imaging system comprises the probe 100 and a transponder sensor 20. A "delay-and-sum" beamforming method may be applied to generate an ultrasound image of the surrounding medium (tissue). In this imaging mode, ultrasound is transmitted from a probe/transducer array (could be multiple transmits with different transmit patterns), and the medium/tissue scattering signal is received by the transponder sensor/sensors to form an ultrasound image. Signals from multiple transponder sensors, or signals from the same sensor but at different locations, can be coherently combined to form the ultrasound image. The locations of the transponder sensors are known or can be calculated at the time of signal acquisition. The transponder sensor can be a "point like" sensor 20a such as a fiber end Fabry Perot cavity sensor and/or a line type sensor 20b or 20c, such as a polarization sensitive fiber sensor. In the case of a "point like" transponder sensor 20a, a delay used to calculate the delay-and-sum beamforming corresponds to a straight-line distance from each pixel (or voxel in 3D imaging) to the transponder location (e.g., see FIG. 4A). In the case of a straight "line type" transponder sensor 20b, a delay used to calculate the delay-and-sum beamforming corresponds to an orthogonal line distance from each pixel (or voxel in 3D imaging) to the transponder sensor 20b line location (e.g., see FIG. 4B). If the "line type" transponder is curved, there may be multiple delay values for each pixel (or voxel) since there may be multiple orthogonal line paths from it to the transponder line sensor 20c (e.g., see FIG. 4C). In some configurations, the line type sensor 20b and/or 20c is a simpler front-end design, optical detection is performed on the back end (e.g., using a polarization analyzer), and/or wavelength locking may not be required. By knowing a position of the fiber with respect to the probe 100, and/or a timing sequency of emitters in the probe 100, a location of tissue scattering can be calculated based on a propagation time of the acoustic signal (e.g., assuming the scattering signal is incident orthogonal to the optical fiber).

Various methods exist for determining the location of the transponder sensor 20 based on the various signals and combinations of signals. In some examples, triangulation may be used to determine a position of one or more of the optical sensors. Ultrasound is transmitted from the probe 100, one or more external elements or array, or an in vivo array (e.g., an array for EBUS, EUS, IVUS). The transducers on the probe 100 emit at least two signals with different wavefronts. The transponder sensor 20 location is determined by the interception point of the different transmit wavefronts at respective received pulse timing. The pulse timing for the ultrasound transmission is determined by extracting and matching the known pulse shape from the transponder-received time sequence ultrasound signal. The pulse timing can be extracted when the pulse signal's signal-noise-ratio is higher than a certain number. A matched filter for known pulse shape or a Wiener filter can be used to enhance the pulse detection fidelity.

Figure 3:
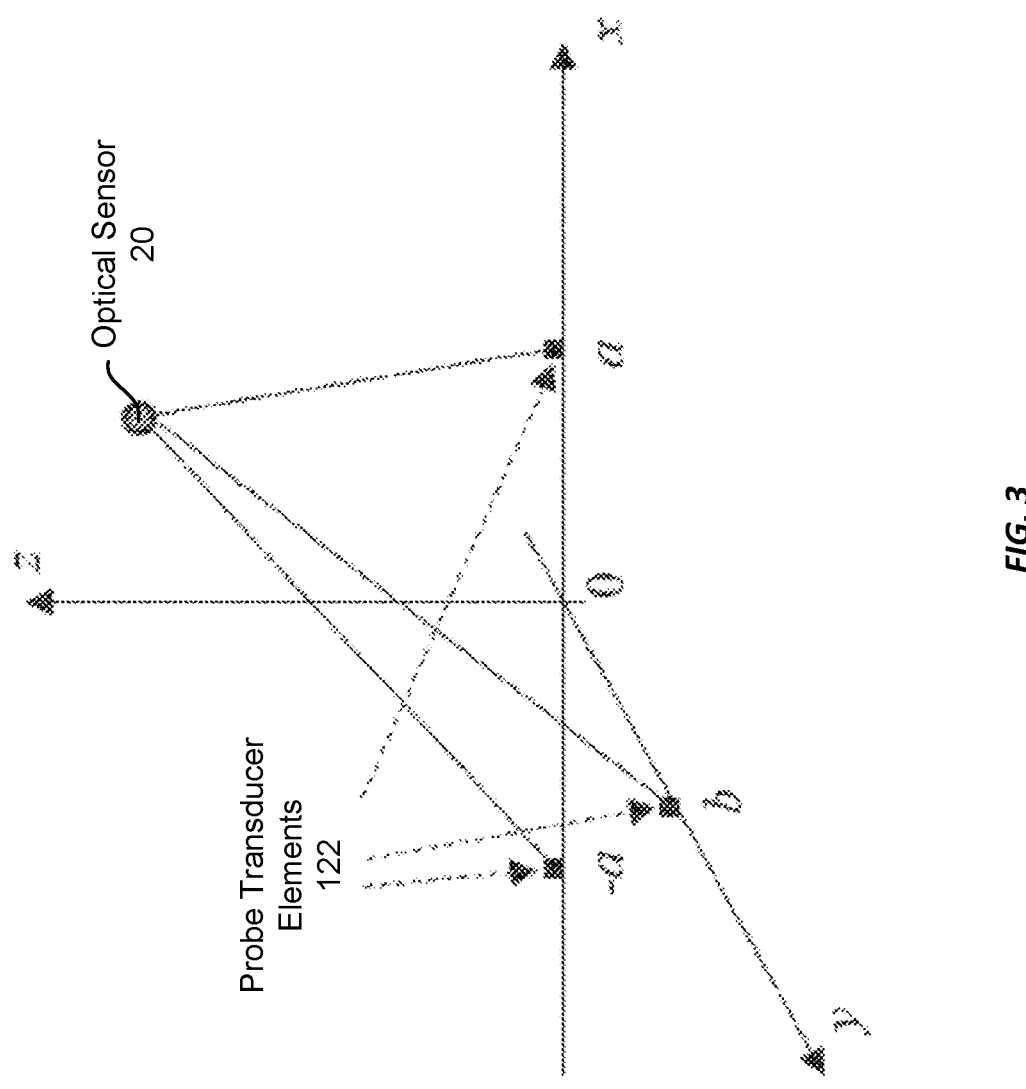
FIG. 3 is a graph illustrating a method of triangulation in one example.

FIG. 3 is a schematic illustrating example positions of probe transducer elements 122 configured to emit acoustic pulses and an example position of an optical sensor 20 in a Cartesian coordinate system. The optical sensor 20 may be arranged on an object (not shown) to be tracked. The location of the transponder optical sensor 20 may be determined using the Cartesian coordinate system as described in the example below. In FIG. 3, three probe transducer element 122 may be configured to emit acoustic pulses. The probe transducer element 122 may form an array (e.g., 1.5D ultrasound array) of a probe (e.g., probe 100). The probe may be configured to emit acoustic beamforming pulses (e.g., using probe transducer elements 122 in FIG. 3) and receive acoustic beamforming signals. Optical sensor 20 may be configured to detect the beamforming signals corresponding to the acoustic beamforming pulses.

In FIG. 3, the three probe transducer element 122 are located at P1: $(-a, 0, 0)$, P2: $(a, 0, 0)$, P3: $(0, b, 0)$, and the optical sensor is located at P: $(x, y, z)$. The distances between the three transducer elements 122 and the optical sensor 20 may be calculated using the following equations:

$$r1 = \left((x+a)^2 + y^2 + z^2\right)^{1/2} \qquad \text{eqn. (2)}$$

$$r2 = \left((x-a)^2 + y^2 + z^2\right)^{1/2} \qquad \text{eqn. (2)}$$

$$r3 = \left(x^2 + (y-b)^2 + z^2\right)^{1/2} \qquad \text{eqn. (3)}$$

Solving Equation 1 and Equation 2 simultaneously results in:

$$x = \left(r_1^2 - r_2^2\right)/4a \qquad \text{eqn. (4)}$$

Equation 4 indicates that $a \neq 0$. That is, the distance between the first element and the second element cannot be zero. Solving Equation 1 and Equation 3 simultaneously results in:

$$y = \left(r_1^2 - r_3^2 - a^2 + b^2 - 2ax\right)/2b \qquad \text{eqn. (5)}$$

x in Equation 5 may be determined from Equation 4. Equation 5 indicates that $b \neq 0$. That is, the third element cannot be on the line determined by the first element and the second element. For example, the first, second, and third elements may form a triangle. Accordingly, the third element is offset in a first dimension (e.g., elevation dimension). Therefore, from Equation 1:

$$z = \left(r_1^2 - (x+a)^2 - y^2\right)^{1/2} \qquad \text{eqn. (6)}$$

where x and y are determined from Equation 4 and Equation 5.

If the acoustic velocity is c and the time required for an acoustic beamforming pulse to travel from the first element to the optical sensor is $t_1$, then:

$$r_1 = ct_1 \qquad \text{eqn. (7)}$$

$r_2$ and $r_3$ may be determined in a similar manner as $r_1$. Therefore, the location of the optical sensor 20 may be determined based on the time required for an acoustic pulse to travel from an element 122 to the optical sensor 20.

Although the location of the optical sensor 20 may be determined by detecting acoustic signals (e.g., echoes) corresponding to acoustic pulses from three probe transducer elements 122, in some examples, more than three elements 122 may be used to determine the location of the optical sensor. The elements 122 may be positioned in any suitable manner. However, in such a triangulation technique, to enable tracking of sensor 20 in a 3D space, elements 122 and the sensor 20 cannot be in the same plane. For example, a first and second element may be arranged along a lateral dimension and a third element may be arranged along an elevation dimension transverse to the lateral dimension where the third element does not intersect the lateral dimension (e.g., so as to be arranged as vertices of a triangle). Accordingly, the third element in this example is not aligned with respect to the lateral dimension of the first and second elements. The first and second elements are offset with respect to each other but are aligned in the lateral dimension.

In some examples, using more than three elements 122 may improve the accuracy of the determined location of the optical sensor 20. In some examples, more than one optical sensor 20 may be used to detect acoustic signals. The position of each optical sensor 20 may be determined similar to as described above. If probe transducer elements 122 and the optical sensor 20 are in the same plane, 2D tracking information within that plane can still be obtained. In this case, at least two transducer elements 122 are used.

In another example, the location of the optical sensor 20 is determined by coherent image forming. Features are most easily identified in ultrasound images when they differ in image brightness. The intensity of the image in ultrasound imaging system is a function of the amplitude of the beam-formed received signal, i.e. the amplitude after coherent addition of the delayed received signal from each transducer element.

In one example, multiple ultrasound firing is transmitted by the external elements or array on the probe 100 and from different locations and/or directions, and with different wavefront (similar to ultrasound imaging transmit sequences). For each pixel in the imaging plane, the pixel values are calculated from the transponder-received signal of the multiple transmissions, with the assumption that the optical sensor 20 is at the location of that pixel. The obtained image (transponder signal image) adds signals coherently only at the true transponder location where the received signal aligns, and ultrasound interference is constructive. The transponder signal image allows transponder sensor 20 position determination because only the transponder location will light up in the image (with the ultrasound physics limiting the transponder image spot size). A single point transponder location can be extracted from the bright transponder spot in the transponder signal image by different methods (e.g., maximal pixel value, median filter, center of brightness weight, etc.). The advantage of using the coherent transponder tracking image is that the received transponder signal from different transmit is first added coherently, and then the pulse timing is determined on the coherently summed signal where the signal-to-noise ratio (SNR) is much higher than a single received time sequence signal. When the external elements/array operate with an imaging firing sequence, an ultrasound image can be generated at the same time of transponder tracking. Thus, there is no dedicated transponder tracking firing sequence. This coherent beamforming transponder imaging method can also be used for 3D tracking of the transponder. In the 3D case, the probe 100 will have (e.g., at least) three probe transducer elements 122, and (e.g., at least) one probe transducer element 122 is outside the plane defined by the optical sensor 20 and another two probe transducer elements 122 of the probe 100 are in plane as shown in FIG. 3.

In one example, the acoustic sensing signal received by the optical sensor 20 from different transducer elements 122 of the probe 100 are summed at the processing system 200 so that a net signal representing the ultrasound signal emitted from each transducer element 122 of the probe 100 is obtained. The sum of the amplitude of the summed signal represents the intensity of the signal received and thus corresponds to the distance along the beam associated with the signal at the angle from the sensor 20 to the probe transducer element 122. Summing of the individual signals is accomplished by providing separate time delay (and/or phase) and gain to the signal from each transducer element 122 in the probe 100. The output signal from the sensor 20 corresponding to each beam forming channel is then coherently added, i.e., each channel is summed, to form a respective pixel intensity value for each beam. The pixel intensity values can be logarithmically compressed, scan converted, and then displayed as an image of the tip of the needle 10 where the sensor 20 is located or the entire needle when multiple sensors 20 are utilized.

In some examples, there can be multiple transponders, such as the sensors 20 coupled to needle 10 in FIG. 2B, each operating and receiving signals independently. The transponder sensors 20 can share or receive the same external elements or array firing sequence signals from probe 100 for tracking each of their respective locations. Coded excitation may be used to increase the signal-to-noise ratio (SNR). Such coded excitation may be used in conjunction with a long or multi-pulse, chirp-signal technique for the ultrasound firing sequences. The received transponder sensor signals can be applied to a matched filter/Weiner filter for pulse compression to achieve a much higher SNR for the pulse timing determination and/or a much better axial resolution in the beamformed transponder signal image. The resulting higher SNR can increase transponder tracking accuracy.

When the transponder includes an emitter 24, the external element or array of the probe 100 can be used to triangulate or beamform to get the transponder location. In such examples, the single point transponder transmits a signal towards the probe 100, and the signal is received by the individual external transducer elements 122 of the probe 100. The position of the transponder can be determined by either triangulation method of coherent transponder tracking image method as described above. Multiple transponder emitters can be used and can transmit at the same time, and each which will show up as a bright spot in the transponder tracking image.

FIGS. 4A, 4B, and 4C depict embodiments of sensing using sensors 20a, 20b, and 20c. In FIG. 4A, sensor 20a, a point-like sensor, is a fiber sensor that can receive scattering from any direction. In FIG. 4B, sensor 20b is a fiber polarimetric sensor that is a straight line receiver. Sensor 20b receives scattering from lateral directions. In FIG. 4C, sensor 20c is a fiber polarimetric sensor that is a curved line receiver. Sensor 20c receives scattering from orthogonal directions. Accordingly, the optical sensor structures, as shown in FIGS. 4A, 4B, and 4C, are configured to detect the acoustic signal across a directional range of at least 180 degrees, at least 270 degrees, at least 300 degrees, at least 330 degrees, or at least 360 degrees.

One or more electrical signals can be generated as sensor data based on one or more detected optical responses to light propagation within one or more optical sensors 20 in response to one or more acoustic signals incident on the one or more sensors 20. The sensor data can be used to enhance an ultrasound image. For example, the probe 100 is used to generate an ultrasound image (e.g., a first image); sensor data is used to generate a sensor image (e.g., a second image; based on known time and location generation of acoustic pulses from the probe 100 and/or a known location of the sensor 20 with respect to the probe 100); and the sensor image is combined with the ultrasound image (e.g., by image fusion using processor 260 in FIG. 1) to enhance the ultrasound image to generate an enhanced image (e.g., a third image; to increase resolution of an area in the ultrasound image near the sensor 20). In some embodiments, sensor data is sent to the processor 260 in FIG. 1 without generating a sensor image (e.g., the processor 260 generates the enhanced image based on the sensor data and data from the probe 100 so that one image, the third image, is generated and the first image and/or the second image is not generated separately from the third image). In some cases, the first image (the ultrasound image) and third image (the enhanced image) are generated without the second image (the sensor image). In some cases, the second image (the sensor image) is generated without generating the third image (the enhanced image) or the first image (the ultrasound image).

A device path can be ascertained by a transponder sensor. When a transponder sensor, or multiple transponder sensors, are integrated on a device (e.g., a needle, catheter, etc.), the location history of the transponder sensor/sensors can be used to determine the path the device has taken. The history path can be used to provide valuable medical information. In some applications, it can be used to predict the device movement. For example, when a needle has travelled a certain distance, using its location history, a projected needle path can be predicted and/or overlayed on the ultrasound image. In doing so, one can assume, in some embodiments, the needle is taking a straight path, or a curved path that can be defined by the history locations. Additionally this information may be used to project the current expected path given the current path. The history path can also be used to indicate the physiological structure the device has gone through. For example, a catheter device travelling through a blood vessel can map the shape of the vessel from the history path of the device transponder sensor. The history path of a device can also serve as records of medical operation and/or to evaluate operation performance and safety. For example, the history of the two transponders on the two sides of a forceps can be used to determine how many times they have closed/opened.

One or more transponder sensors can be used to ascertain the shape and/or orientation of the device. When a transponder sensor or multiple transponder sensors are integrated on a device (e.g., a needle, catheter, etc.), the locations of the transponder sensor/sensors can be used to ascertain the shape and/or orientation of the device. For example, when multiple transponders are integrated along a catheter, their locations can be used to ascertain the shape of the catheter (e.g., point-by-point curve). The shape of the catheter can then be used to ascertain the shape of the physiological structure it is in, for example a blood vessel or a lung bronchus. In another example, the locations of two transponder sensors on a needle can be used to ascertain the orientation and position of the needle (e.g., assuming the needle is a straight line). The locations of three transponder sensors can be used to ascertain the orientation and position of a surface of a medical device (three points form a surface), or the medical device itself if it is a rigid body. When a polarization line sensor is used, multiple transmits can be programmed to emit from a probe to "scan" the line sensor. Since the line sensor is sensitive to ultrasound that laterally arrives at the sensor, the "scan" will generate signals at the sensor when the transmitted ultrasound is lateral to part of the line, therefore locating the section of the line that is lateral to a specific transmit pattern. When the positions and orientations of multiple sections of a line are ascertained from multiple transmit patterns, the shape and position of the line can be ascertained/estimated from the sectional information. The shape and position of the line sensor can therefore be used to indicate the shape and position of a medical device that integrates the line sensor.

Figure 5:
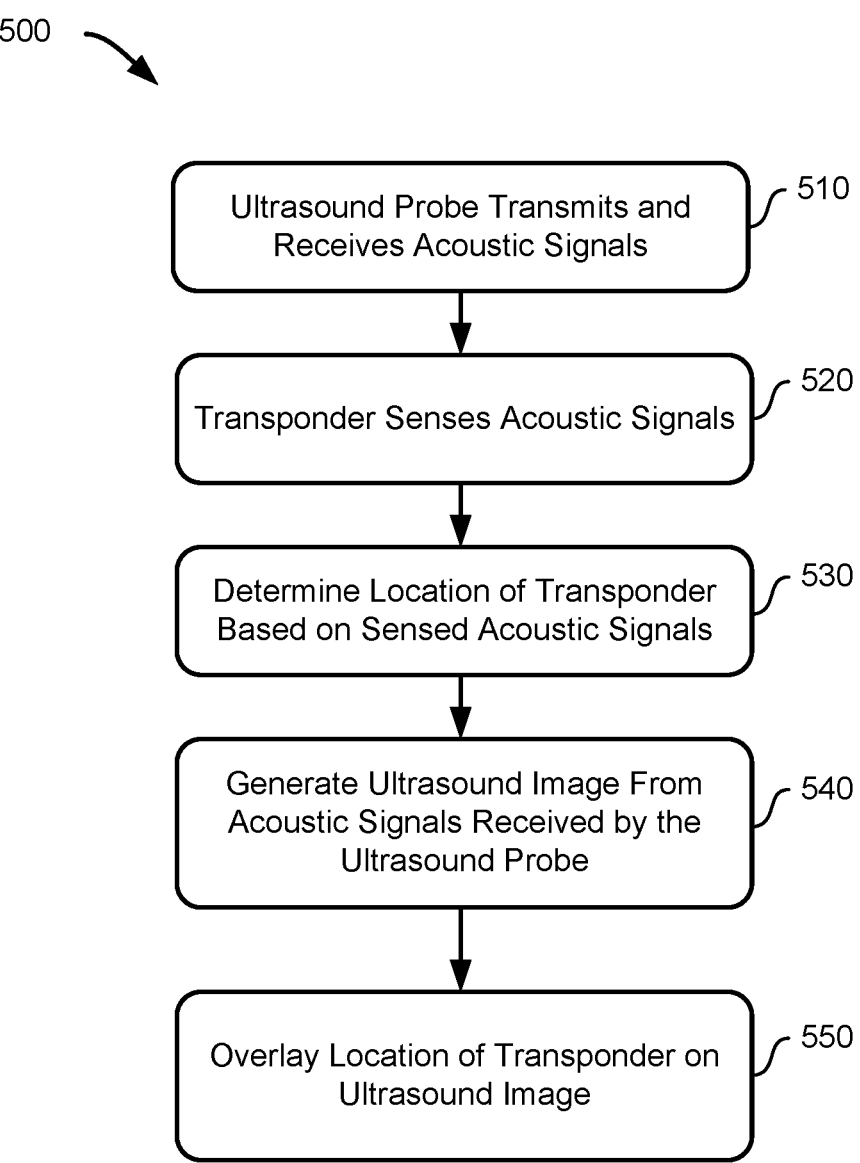

Referring now to FIG. 5, FIG. 5 shows an example method 500 for transponder tracking and ultrasound image enhancement. This example method 500 will be described with respect to the system shown in FIGS. 1 and 2; however, another suitable system according to this disclosure may be employed.

At block 510, an ultrasound probe (e.g., an external or in-vivo probe) transmits and receives acoustics signals. For example, the ultrasound probe 100 shown in FIG. 1 transmits acoustic pulses from an array of transducers into the medium 5, which represents the anatomy of a patient. The probe 100 may transmit these pulses using a variety of known methods or as described above. The probe 100 receives the acoustic signals (e.g., probe 100 receives acoustic signals reflected or scattered from objects and/or features, such as tissue, in the medium 5). For example, echoes might be reflected off of a tumor present in the medium. The probe 100 converts the ultrasound pulses to signals that are then transmitted to the processing system 200.

At block 520, a transponder senses acoustic signals. For example, sensor 20 coupled to needle 10 in FIG. 1 also receives ultrasound pulses that were emitted by the probe 100. The sensor 20 converts the ultrasound pulses to signals that are then transmitted to the processing system 200.

At block 530, the processing system 200 determines the location of the transponder based, at least in part, on the signals received from sensor 20. For example, the processing system 200 may utilize triangulation and/or beamformed transponder signal image method to determine the position of the transponder based on a plurality of signals received from the sensor 20.

At block 540, the processing system 200 generates an ultrasound image. For example, the ultrasound image is generated from acoustic signals received by the probe 100. The ultrasound image may be transmitted to and displayed on the display 300.

At block 550, the processing system 200 overlays the location of the transponder over the ultrasound image. For example, a graphic, such as cross hairs (e.g., "+") or a circle, is overlayed on the ultrasound image to correspond to a location of the needle tip 14 in the ultrasound image. Thus, when viewed by a user, such as an ultrasound technician, medical personal, or patient, the transponder is shown on the same display as the ultrasound image, indicating where in the medium 5, the transponder, sensor 20 on needle 10, is located. The image may also display the path and/or projected path.

Referring now to FIG. 6, FIG. 6 shows an example method 600 for transponder tracking and ultrasound image enhancement. This example method 600 will be described with respect to the system shown in FIGS. 1 and 2. however, any suitable system according to this disclosure may be employed.

At block 610, an ultrasound probe (e.g., an external or in-vivo probe) transmits and receives acoustics signals. (e.g., conventional ultrasound) For example, the ultrasound probe 100 shown in FIG. 1 transmits acoustic pulses from an array of transducers into the medium 5, which represents the anatomy of a patient. The probe 100 may transmit these pulses using a variety of known methods or as described above. The probe 100 receives the acoustic signals (e.g., probe 100 receives acoustic signals reflected or scattered from objects and/or features, such as tissue, in the medium 5). For example, echoes might be reflected off of a tumor present in the medium. The probe 100 converts the ultrasound pulses to signals that are then transmitted to the processing system 200.

At block 620, a transponder senses acoustic signals. For example, sensor 20 coupled to needle 10 in FIG. 1 also receives ultrasound pulses that were emitted by the probe 100. The sensor 20 converts the ultrasound pulses to signals that are then transmitted to the processing system 200.

At block 630, the processing system 200 determines the location of the transponder based, at least in part, on the signals received from sensor 20. For example, the processing system 200 may utilize triangulation and/or beamformed transponder signal image method to determine the position of the transponder based on a plurality of signals received from the sensor 20.

At block 633, acoustic signals are transmitted from a transponder emitter located approximate the distal end of a device towards the probe transducer elements 122. For example, the transponder on the needle 10 shown in FIG. 1 transmits acoustic pulses from an array of emitters 24 into the medium 5. The transponder may transmit these pulses using a variety of known methods or as described above.

At block 636, acoustic signals generated from the emitters 24 approximate the distal end of the device are received by the ultrasound probe. For example, probe 100 receives signals generated by emitters 24. The probe 100 then converts the ultrasound pulses to signals that are then transmitted to the processing system 200. These signals may be in addition to the echoes received by the probe 100 as described, for example, in relation to FIG. 5. The processing system 200 can also determine the location of the transponder based at least in part on the signals received from the probe 100. For example, the processing system 200 may utilize triangulation to determine the position of the transponder based on a plurality of signals received from the probe 100.

At block 640, the processing system 200 generates an ultrasound image. For example, the ultrasound image is generated from acoustic signals received by the probe 100. For example, the ultrasound image is generated using acoustic signals emitted by the probe 100. and the ultrasound image is generated using acoustic signals emitted from the emitters 24. The ultrasound image may be transmitted to and displayed on the display 300. In some configurations, an ultrasound image is generated from acoustic signals transmitted and received by the probe 100, and then the image is modified based on ultrasound pulses received by the probe 100 that were emitted by emitters 24. For example, the processing system may be able to improve the resolution of the ultrasound image, particularly in relation to objects in the medium 5 that are near the transponder.

At block 650, the processing system 200 overlays the location of the transponder over the ultrasound image. For example, a graphic, such as cross hairs (e.g., "+") or a circle, is overlayed on the ultrasound image to correspond to a location of the tip 14 in the ultrasound image. Thus, when viewed by a user, such as an ultrasound technician, medical professional, or patient, the transponder is shown on the same display as the ultrasound image, indicating where in the medium 5, the transponder, sensor 20 on needle 10, is located.

Figure 7:
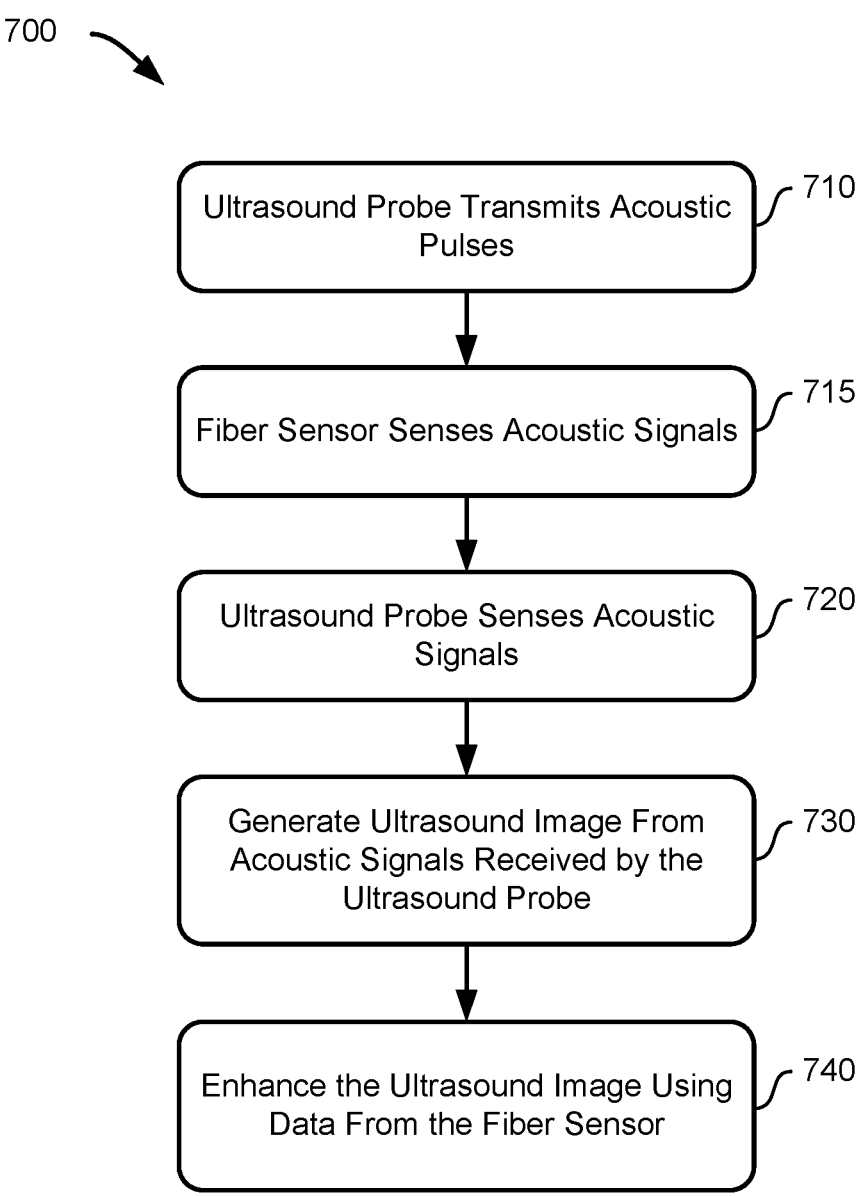
FIG. 7 depicts a flow chart of an embodiment of a method for enhancing an ultrasound image using a point sensor or a line sensor.

Referring now to FIG. 7, FIG. 7 shows an example method 700 for ultrasound image enhancement with a point sensor (e.g., using a fiber end optical sensor) or a line sensor (e.g., using polarization in an optical fiber or multiple point sensors). This example method 700 will be described with respect to the systems shown in FIG. 4; however, another suitable system according to this disclosure may be employed. The fiber sensor 20 can detect scattered signals and tissue harmonics.

At block 710, an ultrasound probe (e.g., an external or in-vivo probe) transmits acoustics pulses. For example, the ultrasound probe 100 shown in FIG. 1 transmits acoustic pulses from an array of transducers into the medium 5, which represents the anatomy of a patient. The probe 100 may transmit these pulses using a variety of known methods and/or as described above. At block 715, the point sensor or line sensor senses the direct acoustic signals (e.g., from a probe 100), acoustic signals reflected and/or scattered from objects and/or features such as tissue in the medium 5, and/or tissue harmonics. For example, echoes might be reflected off a tumor present in the medium 5 in FIG. 1. The point type sensor will receive scattering from any direction or axially as shown in FIG. 4A while the line sensor will receive scattering from orthogonal or transverse directions as shown in FIGS. 4B and 4C.

When a transponder sensor's location is known, the transponder signal can be used together with signals received by elements in the probe (e.g., probe 100 in FIG. 1) for beamforming of ultrasound images, harmonics etc. Transponder sensors can be useful for harmonic imaging of surroundings because transponders are very close to an imaging area of interest, and a harmonic signal is usually weak or unable to propagate very far. Tissue scattering can cause scattering of acoustic signals and/or tissue harmonics. The fiber sensor can detect direct signals (e.g., from a probe), scattered signals, and/or tissue harmonics.

At block 720, the ultrasound probe senses acoustic signals. Signals (e.g., electrical and/or optical from the transducer and/or the probe), that correspond to sensed acoustic signals, are transmitted to a processing system (e.g., system 200 in FIG. 1). In some embodiments, a point-like sensor (e.g., sensor 20 in FIG. 1 or 20a in FIG. 4A) is also used to calculate and overlay a position of a device (e.g., as described in conjunction with FIG. 5).

At block 730, the processing system 200 generates an ultrasound image. For example, the ultrasound image is generated from acoustic signals received by the probe 100 in FIG. 1.

At block 740, the processing system 200 enhances the ultrasound image to generate an enhanced ultrasound image. The processing system 200 uses data from the fiber sensor 20 to enhance the ultrasound image. This data includes the direct signals and scattered signals. The enhanced ultrasound image may be transmitted to and displayed on the display 300. The data from the fiber sensor may also be used to create a separate image of the insonified region surrounding the sensor that is then transmitted to and displayed on display 300.

In some configurations a method comprises receiving, by an optical sensor coupled with a medical device, a plurality of acoustic beamforming signals, each acoustic beamforming signal corresponding to one of a plurality of acoustic beamforming pulses emitted from an ultrasound transducer array; and ascertaining, by a processor, a location of the optical sensor based on one or more of the plurality of acoustic beamforming signals received by the optical sensor. In some embodiments, the method comprises generating an ultrasound image based on acoustic signals detected by an ultrasound receiver array and the plurality of acoustic beamforming signals received by the optical sensor; generating an ultrasound image based on the plurality of acoustic beamforming signals received by the optical sensor; real-time generation of the location of the optical sensor during an ultrasound procedure; tracking a path of the optical sensor based on a history of locations ascertained of the optical sensor based on the plurality of acoustic beamforming signals received by the optical sensor; displaying the path of the optical sensor during an ultrasound-guided procedure; projecting a path of the optical sensor during an ultrasound-guided procedure based on a history of locations ascertained of the optical sensor based on the plurality of acoustic beamforming signals received by the optical sensor; and/or displaying the projected path of the optical sensor during the ultrasound-guided procedure. In some embodiments, the optical sensor comprises a line sensor, a point sensor, or both a line sensor and a point sensor; ascertaining the location of the optical sensor comprises triangulating the location of the optical sensor; ascertaining the location of the optical sensor comprises coherent image forming; one or more sensors are coupled to the medical device to enable real-time generation of a shape or orientation of the medical device during an ultrasound procedure; the optical sensor is one of a plurality of optical sensors coupled with the medical device; and/or the method comprises calculating an orientation of the medical device based on ascertained locations of the plurality of optical sensors.

In some configurations, a system comprises an optical sensor coupled with a medical device and configured to receive a plurality of acoustic beamforming signals corresponding to a plurality of acoustic beamforming pulses emitted from an ultrasound array; and a processor configured to ascertain a location of the optical sensor based on at least some of the plurality of acoustic beamforming signals received by the optical sensor. In some embodiments, the optical sensor is configured to receive a plurality of acoustic signals from a surrounding insonified region; the processor is configured to create an ultrasound image of at least a portion the surrounding insonified region adjacent the medical device based on at least some of the plurality of acoustic signals from the surrounding insonified region received by the optical sensor; the optical sensor comprises a fiber optical sensor; the optical sensor is configured to optically sense a deformation of a material of the optical sensor caused by the acoustic beamforming signals incident on the optical sensor; and/or the optical sensor is configured to detect a polarization change in light guided in the optical sensor as the acoustic beamforming signals are incident on the optical sensor.

In some configurations, a system comprises an optical sensor coupled with a medical device and configured to receive a plurality of acoustic beamforming signals corresponding to a plurality of acoustic beamforming pulses emitted from an ultrasound array, and a plurality of acoustic signals from a surrounding insonified region; and a processor configured to ascertain a location of the optical sensor based on at least some of the plurality of acoustic beamforming signals received by the optical sensor, and create an ultrasound image of at least a portion the surrounding insonified region adjacent the medical device based on at least some of the plurality of acoustic signals from the surrounding insonified region received by the optical sensor. In some embodiments, the processor is configured to present the location of the optical sensor and the ultrasound image in real time; the ultrasound image of at least the portion of the surround insonified region is combined with an image generated by the ultrasound array; and/or the optical sensor comprises a fiber sensor.

In some configurations, a system comprises an optical sensor coupled with a needle and configured to receive a plurality of acoustic signals from a surrounding insonified region; and a processor configured to generate an image of at least a portion the surrounding insonified region adjacent the needle based on at least some of the plurality of acoustic signals from the surrounding insonified region received by the optical sensor. In some embodiments, the optical sensor is configured to receive a plurality of acoustic beamforming signals corresponding to a plurality of acoustic beamforming pulses emitted from an ultrasound array; the processor is configured to ascertain the location of the optical sensor based on at least some of the plurality of acoustic beamforming signals received by the optical sensor; the optical sensor is coupled with the needle at a distal portion of the needle; the optical sensor is arranged on the needle for a diagnostic or therapeutic procedure; the image of at least a portion of the surrounding insonified region is generated in real time; the optical sensor is arranged to detect a change in polarization of light in response to the plurality of acoustic signals; the optical sensor is configured to optically sense a deformation of a material of the optical sensor caused by the acoustic beamforming signals incident on the optical sensor; and/or the optical sensor is arranged to amplify light matter interactions.

While some examples of methods and systems herein are described in terms of software executing on various machines, such as processing system 200, the methods and systems may also be implemented as specifically-configured hardware, such as field-programmable gate array (FPGA) specifically to execute the various methods according to this disclosure. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example one or more non-transitory computer-readable media, that may store processor-executable instructions that, when executed by the processor, can cause the processor to perform methods according to this disclosure as carried out, or assisted, by a processor. Examples of non-transitory computer-readable medium may include, but are not limited to, an electronic, optical, magnetic, or other storage device capable of providing a processor, such as the processor in a web server, with processor-executable instructions. Other examples of non-transitory computer-readable media include, but are not limited to, a floppy disk, CD-ROM, magnetic disk, memory chip, ROM, RAM, ASIC, configured processor, optical media, magnetic tape or other magnetic media, or any other medium from which a computer processor can read. The processor, and the processing, described may be in one or more structures, and may be dispersed through one or more structures. The processor may comprise code to carry out methods (or parts of methods) according to this disclosure.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or examples of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
providing a tracking and imaging system comprising (i) an optical sensor coupled to a medical device, (ii) an ultrasound transducer array, and (iii) a processor;
detecting, by the optical sensor through a photo-elastic effect or physical deformation, a plurality of acoustic signals from any direction, the optical sensor comprising a point sensor for receiving the plurality of acoustic signals from any direction, the plurality of acoustic signals corresponding to one or more of direct acoustic pulses emitted from the ultrasound transducer array, scattered acoustic signals, and acoustic tissue harmonics, the plurality of acoustic signals causing a spectral shift or polarization change in light guided in the optical sensor;
ascertaining, by the processor, a location of the optical sensor based on one or more of the plurality of acoustic signals using coherent image forming, the coherent image forming comprising:
determining a pixel value for a corresponding pixel in an imaging plane based on the plurality of acoustic signals assuming the optical sensor is located at the corresponding pixel to obtain a coherent signal image; and
extracting the location of the optical sensor from the coherent signal image; and
generating, by the processor, an ultrasound image based on acoustic echo signals detected by the ultrasound transducer array and the plurality of acoustic signals detected by the optical sensor.

2. The method of claim 1, further comprising generating a shape or orientation of the medical device based on the plurality of acoustic signals during an ultrasound procedure.

3. The method of claim 1, wherein the optical sensor is an optical resonator comprising a Fabry-Perot resonator, a whispering gallery mode resonator, micro-ring, micro-toroid, spiral resonator, or a photonic crystal resonator.

4. The method of claim 1, wherein the optical sensor is an optical interferometer comprising a Mach-Zehnder (MZ) interferometer, a Fabry-Pérot interferometer, a phase-shift coherent interferometer, or a self-mixing interferometer.

5. The method of claim 1, wherein the optical sensor comprises a fiber end facet, the fiber end facet comprising acoustically responsive metasurface patterns, acoustically responsive low-dimensional materials, or plasmonic structures patterned to amplify light-matter interactions.

6. The method of claim 1, further comprising overlaying the location of the optical sensor on the ultrasound image.

7. The method of claim 1, wherein the optical sensor and the medical device are located within a body of a subject.

8. A system comprising:

an optical sensor coupled to a medical device and configured to detect, through a photo-elastic effect or physical deformation, a plurality of acoustic signals from any direction, the optical sensor comprising a point optical sensor for receiving the plurality of acoustic signals from any direction, the plurality of acoustic signals corresponding to one or more of direct acoustic pulses emitted from an ultrasound transducer array, scattered acoustic signals, and acoustic tissue harmonics, the detected plurality of acoustic signals causing a spectral shift or a polarization change in light guided in the optical sensor; and a processor configured to:

ascertain a location of the optical sensor based on at least some of the plurality of acoustic signals using coherent image forming, the coherent image forming comprising:

determining a pixel value for a corresponding pixel in an imaging plane based on the plurality of acoustic signals assuming the optical sensor is located at the corresponding pixel to obtain a coherent signal image; and extracting the location of the optical sensor from the coherent signal image; and generate an ultrasound image based on acoustic echo signals detected by the ultrasound transducer array and the plurality of acoustic signals detected by the optical sensor.

9. The system of claim 8, wherein the optical sensor comprises a fiber optical sensor.

10. The system of claim 8, wherein the optical sensor is configured to optically sense a deformation of a material of the optical sensor caused by at least one of the plurality of acoustic signals incident on the optical sensor.

11. The system of claim 8, wherein the optical sensor is configured to detect the polarization change in the light guided in the optical sensor as at least one of the plurality of acoustic signals are incident on the optical sensor.

12. The system of claim 8, wherein the processor is configured to:

present the location of the optical sensor and the ultrasound image in real time.

13. The system of claim 8, wherein the optical sensor is coupled with the medical device at a distal portion of the medical device.

14. The system of claim 8, wherein the optical sensor is arranged on the medical device for a diagnostic or therapeutic procedure.

15. The system of claim 8, wherein the optical sensor is arranged to detect a change in polarization of light in response to the plurality of acoustic signals.

16. The system of claim 8, wherein the optical sensor is arranged to amplify light matter interactions.

17. A method comprising:

providing a tracking and imaging system comprising (i) an optical sensor coupled to a medical device, (ii) an ultrasound transducer array, and (iii) a processor;

detecting, by the optical sensor through a photo-elastic effect or physical deformation, a plurality of acoustic signals across a 3D directional range of up to 360 degrees, the optical sensor configured to receive the plurality of acoustic signals across the 3D directional range of up to 360 degrees, the optical sensor comprising a point-like optical sensor, each of the plurality of acoustic signals corresponding to one of a plurality of acoustic pulses emitted from the ultrasound transducer array, the plurality of acoustic signals causing a spectral shift or polarization change in light guided in the optical sensor;

ascertaining, by the processor, a location of the optical sensor based on one or more of the plurality of acoustic signals by coherent image forming, the coherent image forming comprises:

determining a pixel value for a corresponding pixel in an imaging plane based on the plurality of acoustic signals assuming the optical sensor is located at the corresponding pixel to obtain a coherent signal image; and extracting the location of the optical sensor from the coherent signal image; and generating, by the processor, an ultrasound image based on acoustic echo signals detected by the ultrasound transducer array.

18. The method of claim 17, wherein the optical sensor further comprises a line sensor.

19. The method of claim 17, wherein ascertaining the location of the optical sensor comprises triangulating the location of the optical sensor.

20. The method of claim 17, wherein ascertaining the location of the optical sensor based on the one or more of the plurality of acoustic signals comprises ascertaining the location of the optical sensor in real time during an ultrasound procedure.

21. The method of claim 17, comprising:

tracking a path of the optical sensor based on a history of locations ascertained of the optical sensor based on the plurality of acoustic signals received by the optical sensor; and displaying the path of the optical sensor during an ultrasound-guided procedure.

22. The method of claim 17, comprising:

projecting a path of the optical sensor during an ultrasound-guided procedure based on a history of locations ascertained of the optical sensor based on the plurality of acoustic signals received by the optical sensor; and displaying the path of the optical sensor during the ultrasound-guided procedure.

23. The method of claim 17, wherein:

the optical sensor is one of a plurality of optical sensors coupled with the medical device; and the method comprises calculating an orientation of the medical device based on ascertained locations of the plurality of optical sensors.

24. The method of claim 17, wherein the point-like optical sensor has a dimension close to or smaller than a wavelength of an acoustic signal of the plurality of acoustic signals or a diameter of the medical device, wherein the point-like optical sensor is disposed on an optical fiber, at an end of the optical fiber, or adjacent to the end of the optical fiber.

* * * * *